United States Patent
Defemme et al.

(10) Patent No.: US 10,857,067 B2
(45) Date of Patent: Dec. 8, 2020

(54) DEVICE FOR DISPENSING LIQUID FROM A STERILE PACKAGING BOTTLE WITH BI-FUNCTIONAL MEMBRANE

(71) Applicant: Laboratories Thea, Clermont-Ferrand (FR)

(72) Inventors: Alain Defemme, Chamalieres (FR); Fabrice Mercier, Clermont-Ferrand (FR)

(73) Assignee: Laboratories Thea, Clermont-Ferrand (FR)

( * ) Notice: Subject to any disclaimer, the term of this patent is extended or adjusted under 35 U.S.C. 154(b) by 342 days.

(21) Appl. No.: 15/562,915

(22) PCT Filed: Mar. 31, 2015

(86) PCT No.: PCT/IB2015/000423
§ 371 (c)(1),
(2) Date: Sep. 29, 2017

(87) PCT Pub. No.: WO2016/156897
PCT Pub. Date: Oct. 6, 2016

(65) Prior Publication Data
US 2018/0078456 A1    Mar. 22, 2018

(51) Int. Cl.
*A61J 1/14* (2006.01)
*B65D 47/18* (2006.01)
(Continued)

(52) U.S. Cl.
CPC .............. *A61J 1/145* (2015.05); *A01N 59/16* (2013.01); *A61J 1/1456* (2015.05);
(Continued)

(58) Field of Classification Search
CPC .......... B65D 47/18; B65D 35/14; A61J 1/145; A61J 1/1456; A01N 59/16; B01D 61/147;
(Continued)

(56) References Cited

U.S. PATENT DOCUMENTS 5,681,468 A    10/1997 Sawan et al.
9,174,777 B2   11/2015 Defemme et al.
(Continued)

FOREIGN PATENT DOCUMENTS

WO    2011/095877 A1    8/2011

OTHER PUBLICATIONS

International Search Report dated Dec. 10, 2015 issued in corresponding PCT/IB2015/000423 application (2 pages).

*Primary Examiner* — Ariana Zimbouski
(74) *Attorney, Agent, or Firm* — Millen, White, Zelano and Branigan, P.C.

(57) ABSTRACT

The invention proposes a biological protection membrane which is mounted, in a device for dispensing liquid from a sterile packaging bottle, across a fluid-circulation duct, in the path of the liquid extracted from the bottle and the outside air which is drawn into the bottle. The membrane (7) is made partially of a hydrophilic material and partially of a hydrophobic material. Both the hydrophobic portion (23) and the hydrophilic portion (22) are made from a polymer base, laden in the body thereof with a biocidal agent that is active in the destruction of bacteria by the ionic oxidation effect. The circulation of fluids through the membrane (7) is organised so as to promote the ionic action on the flow of outside air in the hydrophobic material, and to drive the ionically charged active agent by the liquid passing through the membrane in the hydrophilic portion thereof. A porous buffer (8), inserted in the path of the fluids on the inside of the membrane, collects the active agent extracted from the membrane by the remaining liquid not dispensed, passing through the membrane from the outside towards the inside.

20 Claims, 2 Drawing Sheets

(51) Int. Cl.
*A01N 59/16* (2006.01)
*B01D 61/14* (2006.01)
*B01D 67/00* (2006.01)
*B01D 69/02* (2006.01)
*B01D 71/02* (2006.01)
*B65D 35/14* (2006.01)

(52) U.S. Cl.
CPC ....... *B01D 61/147* (2013.01); *B01D 67/0044* (2013.01); *B01D 69/02* (2013.01); *B01D 71/022* (2013.01); *B01D 71/028* (2013.01); *B65D 35/14* (2013.01); *B65D 47/18* (2013.01); *B01D 2311/2692* (2013.01); *B01D 2323/30* (2013.01); *B01D 2325/36* (2013.01); *B01D 2325/38* (2013.01)

(58) Field of Classification Search
CPC .. B01D 67/0044; B01D 69/02; B01D 71/022; B01D 71/028
See application file for complete search history.

(56) References Cited

U.S. PATENT DOCUMENTS

| | | | | |
|---|---|---|---|---|
| 2009/0286926 A1* | 11/2009 | Yanagisawa | ......... | C08K 5/0083 524/599 |
| 2010/0084397 A1* | 4/2010 | Kubo | ............ | B65D 47/18 220/256.1 |
| 2011/0024355 A1* | 2/2011 | Mansouri | ........... | B01D 67/0079 210/650 |
| 2011/0125111 A1* | 5/2011 | Chibret | ............ | A61F 9/0008 604/300 |
| 2012/0310185 A1* | 12/2012 | Defemme | ............ | A61F 9/0008 604/296 |

\* cited by examiner

DEVICE FOR DISPENSING LIQUID FROM A STERILE PACKAGING BOTTLE WITH BI-FUNCTIONAL MEMBRANE

The invention relates to the technology of bottles intended for the sterile packaging of liquids that must be expelled from the bottle in separate steps over time. It relates more specifically to the provisions that are intended to ensure as far as possible that the sterility of the liquid is maintained throughout the steps of its consumption, focusing both on the liquid that remains in the inner reservoir of the bottle and on that which is expelled therefrom at each step of dispensing from the bottle.

Preferably, but non-limitatively, the invention is utilized in particular in the field of pharmaceutically, or para-pharmaceutically, active liquid compositions, in particular in ophthalmological applications. This is a field in which questions of purity of the product dispensed, and accuracy in discontinuous dispensing, are particularly important. Closely related requirements can also be found for example in cosmetology or in dermatology, in particular with respect to accuracy in positioning the location for expulsion of the drop or the spray from a reservoir for collecting the liquid inside the bottle, as well as, if applicable, compliance with a predetermined dosage to be administered at each dispensing step.

It is known to equip sterile packaging bottles of the flexible-wall type for elastically reversible deformation with an annular head for dispensing liquid which is inserted in a sealed connection into a rigid neck of the bottle to extract the liquid therefrom via a tip projecting to the outside of the bottle and which comprises, across the internal duct, a bacteriological protection membrane capable of acting as a filter with respect to microorganisms having the dimensions of bacteria and thus acting to protect the liquid contained in the bottle from contaminating agents that could enter therein from the outside environment.

Independently of such a protection, it is known that in bottles with elastically deformable walls in general, dispensing of the liquid is ensured by manual compression of the bottle, and that the return of the bottle to its original inflated form causes an entry of air replacing the volume of liquid extracted therefrom. Rather than equipping the bottle with a mechanical valve for managing the alternation between expulsion of liquid and entry of air, it then became common practice to use selective-permeability membranes for this purpose, in an arrangement in which they allow the passage alternately of liquid and of air depending on the pressure differences between one side and the other. Devices are known, in particular from patent documents, in which several membranes are arranged inside the bottle in order to achieve this selective permeability, while in bottles manufactured industrially by the Applicant, in particular according to the French patent application published under number FR 2872137 (corresponding international application WO 2006/000897), such a membrane is arranged across a single duct allowing passage to the flows of air and of liquid between the inside and outside of the bottle, in one direction and in the other.

This operation is made possible due to the fact that a membrane called a bi-functional membrane is used as a single membrane, which is made partly of a hydrophilic material and partly of a hydrophobic material. The particular feature of these membranes is to allow sometimes the aqueous liquid from the bottle, sometimes the outside air, to pass through preferentially, depending on a pressure difference between its two faces, which varies alternately according to whether the fluid pressure is higher or lower on the internal side of the membrane, on its face oriented towards the inside of the bottle, than the pressure exerted on its outer face, oriented towards the outside of the bottle.

The presence of such a membrane, allowing on the one hand the passage of the liquid in the dispensing direction, under the effect of a pressure exerted manually by the user on the deformable wall of the bottle, and on the other hand the passage of the air in the opposite direction, from the outside to the inside of the bottle, when the pressure on the wall is released after dispensing a dose of liquid, represents one of the factors making it possible to package biologically pure liquids in multidose bottles without the need to incorporate preservatives into their composition.

The usual applications involve a dispensing of liquid and aspiration of a back flow of air in the same atmosphere, namely the essentially non-sterile living environment of the consumer. In addition, in a number of applications, ophthalmology for example, it is advisable to pay particular attention to contamination by bacterial agents present on the skin or mucous membranes of the persons undergoing treatment.

Hence the need to further improve antibacterial protection which, according to the present invention, has led to yet another sterility protection function being conferred on the same membrane.

Thus the invention proposes to close the sterile packaging reservoir of the bottle, at the base of a tip for the expulsion of its contents from the bottle, by a membrane that is at the same time a filter for the bacteria or similar microorganisms and a semi-permeable bi-functional membrane with regard to the fluids, the mass of which is also loaded with a biocidal agent acting by the ionic oxidation effect. Such an agent is supplied more particularly by macromolecules bearing positively-charged metal ions, such as those proposed by now well-known prior art in the form of mineral polymers of the amino-silicate family, called zeolites, retaining within them labile metal ions. Among the useful ions are silver ions (Ag+ or Ag++) which have been found to be the most advantageous in an industrial context for antibacterial protective membranes utilized according to the present invention.

The present invention therefore mainly consists of supplying a sterile packaging bottle closed by a biological protection membrane that brings together the three functions, that of filtration membrane, that of bi-functional membrane separating the flows of fluids passing therethrough by distinguishing the air from the liquid, and that of a material loaded with an agent having a biocidal ionic effect on the products coming into contact therewith. In this way, it makes it possible to take advantage of the particular features of the constitution of the membrane in a mode of implementation of the biocidal ionic effect manifesting itself differently according to whether it is exerted in the presence of air or in the presence of liquid.

In order to best ensure the role of such a membrane within the context of its utilization, the invention provides for adding to this main feature various complementary features that combine their effects in the operation of a sterile packaging bottle for liquid, of the type having a wall that is elastically deformable by manual pressure. These features mainly relate to producing the membrane itself, the constitution of the head for dispensing liquid from the bottle in which it is arranged across a wide duct for circulation of the fluids, and on the configuration of the rigid elements that frame the membrane across this duct. The features of these three innovations of the invention will be even more effective in achieving a good quality of protection against the biological contaminants in complete safety under normal conditions of use of the bottles when they are utilized in combination with one another.

With respect to the membrane itself, the present invention advantageously provides for it to be made of a hydrophilic porous polymeric material homogenously loaded with an agent having a biocidal effect by ionic oxidation, said material constituting said membrane throughout its entire mass, and then being rendered hydrophobic locally over a part of the extent of the membrane across the duct for the circulation of the fluids between the inside and the outside of the bottle, by an additional polymerization treatment protecting its biocidal activity.

This makes it possible to arrange a suitable volume for placing the gaseous phase, constituted by air, in contact with the polymeric material loaded with active ions within the porous mass over the entire thickness of the membrane. The same purpose is served by the fact that the hydrophilic base material of the membrane is constituted in a finely homogeneous manner, which excludes earlier realizations of filter membranes made of a filament-based material retaining charged particles between the fibres. According to the invention, it is preferred to start from a molten polymer base comprising fusible granules of a masterbatch, itself incorporating mineral macromolecules bearing active ions.

Whereas conventionally, filtration of the bacteria requires a fine porosity, not exceeding 0.2 µm, the presence of a biocidal agent within the membrane makes it possible to protect sterility satisfactorily with coarser porosities, preferentially of around 0.3 or 0.4 µm, or more widely up to 0.5 µm, or even up to 0.6 or 0.7 µm, or even 1 µm, which is advantageous from the point of view of pressure losses and allows viscous liquids to be treated. In practice, the invention also makes provision, according to a preferred embodiment, for producing the membrane such that it has an average pore diameter adapted for filtering out microorganisms having dimensions greater than a particle size comprised between 0.3 and 1 µm, in particular between 0.3 and 0.6 micrometre.

The support macromolecules of the active biocidal ions are advantageously, as has already been indicated, mineral polymers of the aluminosilicates type, in which the active ions are incorporated, more specifically, in a manner known per se, being metal ions such as silver ions or similar metals in ionic form, which bind to the free sites of the polysiloxane chains via polar covalent bonds. These mineral polymers are preferably crystalline polymers. Without restricting the conditions of application of the invention, the active ions concentration in the membrane is preferably chosen comprised between 100 and 100,000 ppm, taking as an example the case of a mineral polymer based on aluminosilicates bearing silver ions in a membrane with a porosity of approximately 0.2-0.3 micrometre.

Attention will now be given to the advantageous features of the invention relating to the device for dispensing liquid from a sterile packaging bottle according to the invention, in which a membrane constituted as above is mounted across a duct for the circulation of the fluids between the inside and the outside of the bottle.

More particularly, means will be discussed for organizing the circulation of the air and liquid fluids through said membrane that the device comprises in combination therewith, after recalling that the membrane, bi-functional in this respect, is then arranged in the duct for the circulation of the fluids between a part with a wide cross-section situated in a nacelle or insert for sealed connection with the bottle, upstream of the membrane (with respect to the direction of the outflowing liquid), and a channel with a capillary cross-section passing through a tip extending said nacelle from the bottle as far as an orifice for the ejection of the liquid. Along this channel, situated downstream of the membrane, the air and liquid fluids circulate alternately, either to leave the bottle or to enter therein. In fact, in applications of this type, during operation, the membrane acts as a flow separator by distinguishing the liquid and the air reaching it in the mixtures thereof, due to its being partially hydrophilic, i.e. selectively permeable to the liquid in the presence of air, and partially hydrophobic, i.e. selectively permeable to air in the presence of liquid.

Among the features in question is the fact that in the base of the tip adjacent to the membrane on the outer side, are arranged respective means for guiding the air aspirated from outside and any remaining liquid that has not been dispensed and is required to return to the bottle, which are configured, in proximity to the membrane, so as to promote a biocidal effect on the aspirated airflow being exerted inside the membrane, within the hydrophobic porous material, and rather promoting entrainment of the biocidal agent from the membrane by the flow of liquid passing therethrough in its hydrophilic part. In a preferred embodiment example of the invention, this is achieved by guiding means that tend, in particular by grooves cut radially into the material of the tip, to turn away towards the part of the remaining extent of the membrane that has hydrophilic properties, any flow of liquid preceding the outside air aspirated via the channel of the tip, and which tend conversely, thanks optionally to additional corrugations that are more shallow than said slots, to finely divide the airflow while concentrating it on the part of the extent of the membrane rendered hydrophobic, this hydrophobic part being advantageously provided facing the channel of the tip for this purpose.

It will be noted here that the effect of the biocidal agent with an ionic load cannot be differentiated according to whether it affects a flow of liquid or a flow of air, via a membrane made in multiple layers, even assuming that among a series of superimposed layers, whether made of porous fibrous or non-fibrous material, there is included a hydrophobic layer or a hydrophilic layer, or even a hydrophobic layer and a hydrophilic layer, since zones having specifically hydrophilic or hydrophobic properties of the membrane would inevitably be incapable of separating the flows by distinguishing the liquid and the air in the overall flow reaching them.

According to yet further features of the invention, the means for organizing the circulations of the fluids in the device for dispensing liquid from a sterile packaging bottle comprise a porous plug mounted across the duct for the circulation of the fluids in the nacelle or insert, i.e. upstream of the membrane, which is made of a material capable of receiving and absorbing the biocidally active agent entrained by the liquid out of the membrane while preventing its entry to the inside of the bottle. In the knowledge that such plugs are known in their function as flow regulators by the creation of a pressure drop in the path of the liquid pushed out of the bottle, provision is made by the present invention to make them play a new role in the protection against contaminants of sterility, by designing them so that they constitute a reserve of active agent for the destruction of bacteria.

To the extent that the material constituting the plug has not been loaded with biocidal agent during manufacture, the available reserve of active agent is only constituted as from first use of the bottle during consumption of its contents. Therefore, in conjunction with the particular features of this material, in particular its nature and porosity, which affect its capacity for retention of the biocidal agent and the lifetime thereof, the axial length of the plug through which the fluids pass both outwards and inwards can be determined, without any particular difficulty, by persons skilled in the art, so that the bio-destructive agent is progressively collected therein, starting with the layers on the outer side, without being able to reach the last layers on the inner side. Thus there is not the slightest risk of contamination of the internal environment of the bottle, at least throughout the entire normal period of use of the bottle until its contents have been completely consumed.

It will be noted that such a porous plug does not need to play the same roles of filtering element or flow separator as the membrane, since it is located in the part of the duct for the circulation of the fluids where the air and liquid are free to mix together. It follows that in the embodiments of the invention that are the most advantageous in practice, the plug is constituted on the basis of compacted fibrous material. This material preferably has hydrophobic properties, to the extent that the porosity is also relatively coarse.

If appropriate, it is possible to further improve the result of the joint biocidal activity of the membrane and of the porous plug, by completing the design of the device according to the invention with features that are known per se, which relate to constitution of the tip for the expulsion of the liquid extracted from the bottle, paying special attention to applications of the invention to dropper-tip bottles such as those used for liquids to be dispensed in a downward direction as is common practice in ophthalmology. Thus there is benefit in particular in utilizing embodiments where the tip for the expulsion of the doses of liquid is constituted by a material that is itself loaded with biocidal agent, as was described in particular in international patent application WO 10/013131 (also published as patent application US 11/0125111), which makes it possible to act on the fluids already outside the membrane, where the air and liquid fluids circulate alternately in a narrow central channel of the tip.

Overall, the cooperation of the successive biocidally active structures in the path of the fluids safeguards the sterility so that it is possible to substantially reduce the antibacterial quality requirements of the membrane in terms of filtration. While a filtration quality is usually prescribed that is expressed by a porosity from 0.1 to 0.2 µm (average pore diameter), it becomes advantageous, according to the invention, to set this porosity at a value comprised between 0.3 and 1 µm, or better still, between 0.4 and 0.6 or 0.7 µm, as has already been indicated. The pressure drop undergone by the liquid on passing through the membrane is thereby substantially reduced, which may make it possible, subject to increasing the pressure drop on passing through the flow-regulator plug by the same amount, to increase the axial length of this plug, and thereby to improve its role in retaining the ionic loads available in their biocidal activity for an additional treatment of the fluids passing into its pores. But a coarser porosity of the membrane is in itself also very useful in opening up further possibilities in the industrial application of the bottles, to the extent that their operation will be less sensitive to the viscosity of the packaged liquid. Thus provision is made to utilize the bottles designed and constructed according to the invention for packaging polymer-based eye drops, the consistency of which is similar to that of gels.

The invention will now be described in greater detail within the context of preferred features and their advantages, focusing on a particularly suitable embodiment for packaging an aqueous solution such as eye drops, with reference to FIGS. 1 to 5.

Figure 1:
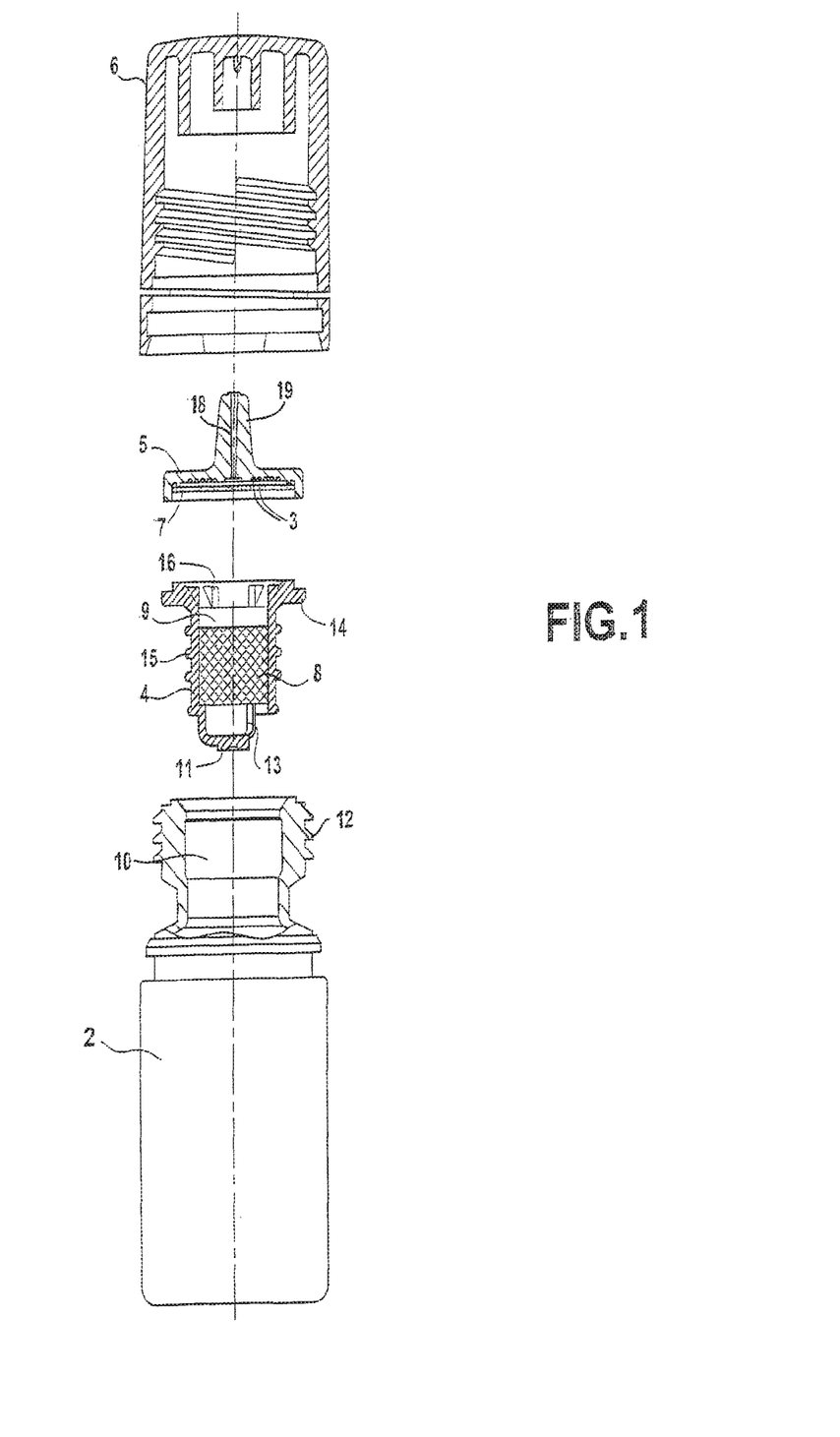
FIG. 1 shows, in an exploded view in longitudinal section, the various elements of a sterile packaging bottle with a deformable wall, that is equipped with a device according to the invention for dispensing a liquid to be expelled from the bottle in successive doses through a bacteriologically protective membrane, until the liquid that it contains, in a sterile state at the time of first use thereof, has been used up.

In its general construction and as shown in all its elements in FIG. 1, the bottle described appears to conform to the usual design for sterile packaging bottles in the applicant's earlier patents. However, it differs therefrom by features specific to the invention that are distributed over its constituent elements essential for dispensing under bacteriological protection ensured according to the invention, namely the membrane (7), the porous plug (8) occupying the internal space in the nacelle (4), and the base (3) of the tip (5) for dispensing liquid from the bottle (2) as well as their relative assembly associated with the circulation of the fluids through the membrane.

According to the invention, the membrane that the bottle for dispensing eye drops in a sterile state contains is used for separating the air and liquid flows that pass therethrough, as a bacteriological protection membrane by filtration and, by the fact that its material contains mineral macromolecules bearing silver ions with a biocidal effect by ionic oxidation, for the destruction of the bacteria or similar microorganisms in the fluids that pass therethrough.

Once mounted in the bottle, at the interface between the inside and the outside of the bottle, it forms part of an assembly for organizing the circulation of the fluids therethrough that results in an alternation of the flows of liquid and of air in the expulsion channel with a narrow flow section that is arranged in the centre of the part of the tip (5) that is tapered in the form of a cannula (19), here configured as a dropper dispenser. The circulation of the fluids is alternated downstream of the membrane on the expulsion circuit, whereas upstream, the air and the liquid are mixed in the duct with a large flow section that precedes the membrane in the nacelle (4) for sealed connection of the assembly onto the bottle, in its neck (10).

Inside this duct, upstream of the membrane on the inner side of the bottle, there is also a porous plug (8) one of the functions of which remains that of flow regulator involved in organizing the flows through the membrane by creating a pressure drop in the path of the liquid leaving the bottle. During operation, the membrane may equally well be in the presence of air or of liquid during liquid dispensing operations. The same plug also has a role, according to the invention, of acting as a plug with respect to the transfer of ionic loads that are active in the destruction of bacteria. It collects them from the liquid that flows back towards the inside of the bottle (2) and retains them in the porous material, so that the biocidal activity is available there to continue the action of destroying bacteria, also with respect to the air entering the bottle in compensation for the dose of liquid that has been expelled therefrom.

According to the invention, the membrane (7) is constituted homogeneously throughout its entire mass as regards the distribution of the crystalline polymer supporting the biocidal ions, more particularly here a zeolite loaded with silver ions. In order to ensure this homogeneity both in the part of the membrane that is hydrophilic (22 in FIG. 5) and in that which is hydrophobic (23 in FIG. 5), a choice was made to make the membrane of a polymeric material based on polyester resin modified by a polyamide or polyethersulfone resin that is shaped in the molten state after the zeolite has been incorporated therein.

Figure 5:
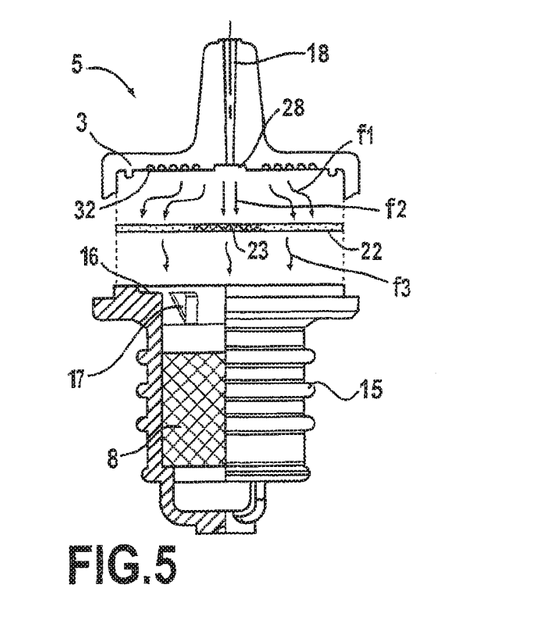
FIG. 5 shows the operation of the bacteriological protection membrane in conjunction with that of the porous plug absorbing the biocidal agent in the return path of the fluids to the inside of the bottle after expulsion of a dose of liquid.

The degree of polymerization of the base polymeric material and the porosity and thickness characteristics are then such that they result in a membrane with hydrophilic properties. Then the material is rendered hydrophobic in its mass throughout the entire thickness of the membrane, but locally in a defined zone of the extent of its surface. This zone constitutes the hydrophobic part of the membrane whereas the rest of its extent retains its hydrophilic nature. Local exposure to irradiation under ultraviolet radiation, represents a good way of modifying the structure of the polymer in situ by radical crosslinking reactions between its constituents, while maintaining the properties of the active ions imprisoned in the zeolite.

In operation, during the operations of dispensing the doses of liquid from the bottle, the structure of the membrane, in conjunction with the organization of the circulation of the fluids therethrough, tends to promote an action that destroys the microorganisms by ionic oxidation that is exerted on the airflow within the hydrophobic material itself by contact between the air and the polymer loaded with ions at the surface of the pores, while conversely, in the hydrophilic part of the membrane, the biocidal ionic load tends to be entrained by the liquid passing through the membrane.

The inflow of air through the tip of the bottle is a gaseous fluid that comes directly into contact with the biocidal ions within the pores and thus reacts immediately with the biocidal agent, while the remaining liquid returning to the bottle does not consume in situ the entire ionic load that it is capable of extracting from the material of the membrane, so that the flow of liquid returning to the inside of the bottle entrains with it any ionic load that may be available in order to carry out its biocidal activity further on.

The result presents a real advantage by the efficacy of the destruction of the bacteria ensured on the air coming from the outside which is thus mostly treated before entering the bottle. As regards the hydrophilic zone through which the liquid passes, it is more important that the ionic effect persists in the liquid re-aspirated towards the inside of the bottle. The ionic load is then collected and retained in the porous material of the porous plug (8) to the extent that the biocidal ions are not consumed in the gap existing inside the nacelle between the membrane and the plug. Across the duct for the circulation of the fluids between the inside and the outside of the bottle, upstream of the membrane, the ions are then available there to act on any remaining organic contaminant reaching there.

It should be noted that the axial length of the plug in the path of the fluids is chosen to be sufficient so that the biocidal ions are never entrained therethrough as far as the inner reservoir of the bottle. In practice, the choice of the dimensional features of the plug and its porosity, as well as the choice of the gap free of material separating it from the membrane in the nacelle, are the result of a compromise between the needs of the circulation of the fluids in terms of pressure and those pertaining to the effects of the initial ionic load of the membrane. In the particular case described, the plug is made of polyester-based polymeric material, more particularly polyethylene-based, which is formed with hydrophilic properties and porosity of the order of 100 μm, more generally comprised between 20 and 150 μm in average pore diameter. Its length along the axis of the bottle is comprised between 3 and 10 mm. Its distance to the membrane in question on its face inside the bottle is of the same order of magnitude.

On this side, upstream of the membrane in the wide part of the duct for the circulation of the fluids provided by the annular shape of the nacelle 4, the free surface of the membrane is clear. However, supporting fins (16 and 17 in FIG. 5) are formed on the nacelle, on the inside, to limit the stresses that could be exerted, during operation, on the periphery of the membrane where it is fixed bonded on a peripheral ring of the base of the tip for expulsion of the liquid, but they leave the membrane free to curve away from the base (3) of the tip.

Opposite the external face of the membrane viewed with respect to its hydrophilic nature, the base (3) of the tip (5) forms a supporting surface for the membrane during the liquid expulsion phases, which joins the wall of the central expulsion channel (18) at the level of its flared nozzle (28).

Around this nozzle, the free surface of the tip is scored with radial slots offering a wide cross-section for passage of the liquid in proximity to the membrane on the outside of the bottle. These slots, arranged radially, are shown as 31 in the front view of FIG. 4. Their role is to collect the liquid leaving the bottle and guide it to the nozzle of the expulsion channel after it has passed through the membrane in its hydrophilic zone, but their role is also, with respect to the non-expelled remaining liquid that is aspirated back to the bottle in the air-entry phase compensating for the expelled liquid, to facilitate its being directed, under the pressure of the air, to the hydrophilic zone (22, FIG. 5) freeing the central hydrophobic zone (23, FIG. 5) for the air that then arrives above Furthermore, the surface of the base (3) has corrugations that tend to finely divide any path for the circulation of air arising at the outlet of the nozzle of the capillary channel of the tip, which tends to reduce the speed at which it then crosses the membrane, despite the latter being pushed away from the transversal surface of the base of the tip.

In the preferred embodiment of a tip thus produced according to the invention, in particular in the case of a dropper tip, in which it is important, for the quality of the formation of the drop, for air not to be mixed with the liquid in the drop expulsion channel, the corrugations dividing any air circulation path are present in the form of grooves (32, FIG. 4) which are relatively narrow and not very deep, thus having a fine flow section, which are each annular and distributed in a concentric arrangement with respect to one another around the central capillary channel of the tip. These grooves (32) are cut into the surface of the base of the tip, in the sectors of the base retained by the slots (31) for guiding the flow of liquid, at the point where the surface of the base of the tip is rather reserved to act as a bearing support for the membrane when the latter is pushed by the internal pressure of the compressed bottle in order to expel liquid.

It is understood that during operation, the particular configuration of the surface of the tip facing the membrane plays an important role in the organization of the circulation of the fluids, not only by promoting an alternation between liquid flow and gaseous flow in the central channel of the tip, but also by guiding the fluids on their return path as shown by the arrows in FIG. 5. The arrows f1 show that the non-expelled remaining liquid that is returned first is diverted from a direct axial path and oriented towards the hydrophilic part of the membrane (22). It is thus prevented from being sprayed onto the central part of the membrane, where it would tend to wet the material of the membrane, which has a hydrophobic character in this area. The flow of aspirated air towards the bottle thereby has free access to the hydrophilic material of the membrane in its central portion (23), as shown by the arrows f2.

Figure 2:
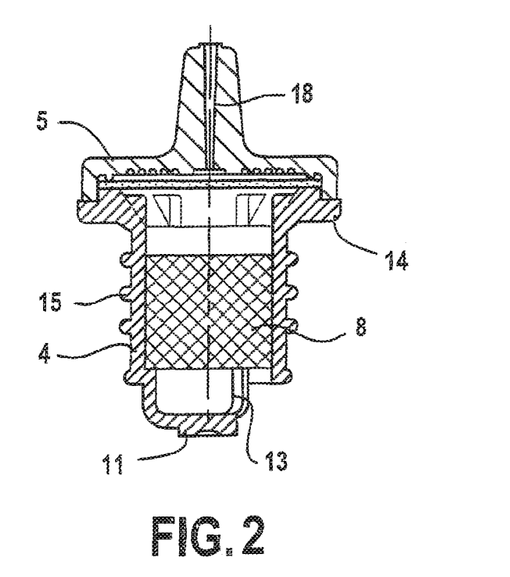
FIG. 2 more particularly shows the dispensing device in longitudinal cross-section, once its specific elements are assembled to constitute a head for dispensing liquid and entry of outside air, for insertion in the neck of the bottle.
Figure 3:
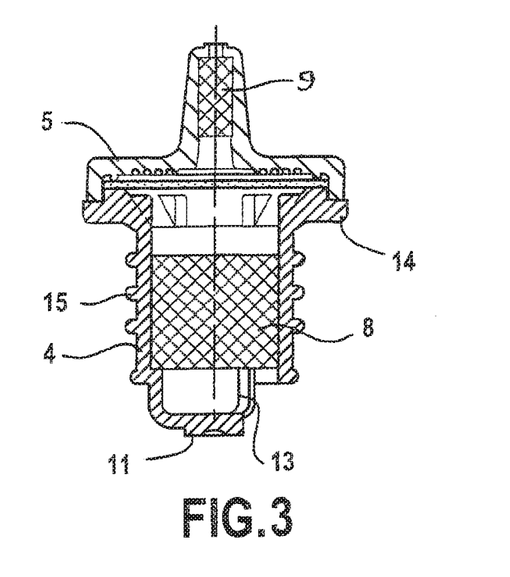
FIG. 3 shows, in longitudinal cross-section, an embodiment variant of the head for dispensing liquid of FIG. 2.
Figure 4:
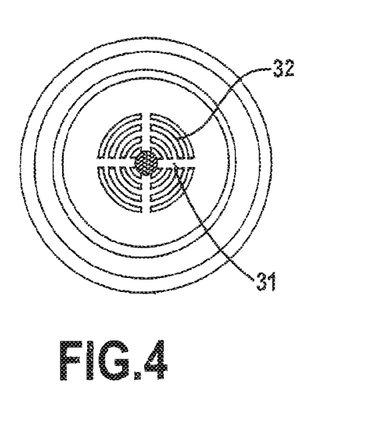
FIG. 4 shows the configuration of the base of the tip on its surface located facing the nacelle.

Referring now to FIGS. 2 and 3, emphasis will be placed on the preferred embodiments of the invention, in which the membrane loaded with Ag ions combined with the porous plug receiving the same ions, in addition combines the effects thereof with those of a tip, itself made of a material loaded with biocidal agent, here also supplied by an ion-supporting zeolite filler.

A dispensing head the tip of which is thus loaded with biocidal agent while the material constituting the nacelle is devoid thereof is sufficiently described in the Applicant's prior patent WO2010/013131, making more detailed description unnecessary here. The same applies for the variant in FIG. 3, in which the porous core 9 is noted, made of a hydrophobic polymeric material, which occupies the internal space of the expulsion channel 18. The purpose of this central core is to divide the gaseous flow by promoting its contact with the intrinsic free surface without thereby excessively slowing the circulation in the case of a liquid flow. When the material constituting the core is loaded with biocidal agent, in particular of an ionic-silver-supporting zeolite, the destructive effect on bacteria is thereby promoted, exerted on the outside air as soon as it arrives at the tip.

Regardless of the part of the tip that is loaded with biocidal ions, the tip itself or a porous core in the central channel (or also other means for dividing the flows as has been described in the patent texts already mentioned), it is remarkable that in the entire dispensing head, the tip constitutes a source for re-supplying the bacteriological protection membrane by allowing the ionic load that is active in the destruction of the bacteria, that may have been released therefrom without being completely consumed in situ, to escape towards it, mainly with the liquid flow.

Returning now to FIG. 1, together with FIG. 2, it is possible to observe other details of the realization of the head for dispensing liquid from a sterile packaging bottle which, while themselves being standard features of the bottles manufactured industrially by the Applicant, are nonetheless means involved in the implementation of the present invention due to their property of maintaining sterility in the bottle.

In this respect the presence of external peripheral ribs (15) on the nacelle (4), which ensure sealing against bacteria with the neck of the bottle (10) at the level of the porous plug (8) will be noted. The configuration of the cap (6) will also be noted, which is such that, when it is screwed (at 12) onto the neck of the bottle, it closes the external nozzle of the channel 18. Among other things, its role is to ensure a pressure drop downstream of the membrane that prevents the latter being wetted by the liquid contained in the bottle provided that the tamper-proof ring (26) has not been broken for a first use (first expulsion of an eye drop).

Similarly, the shape of the nacelle (8) at its upstream end, inside the bottle, will also be noted. Its utility will become apparent firstly, in embodiments intended for dispensing eye drops with surface-active or viscous physico-chemical features, and in such cases the means shown will advantageously be exploited in combination with more specific embodiments of the invention, namely those providing for a membrane having a relatively coarse porosity leading to a lower protection from microorganisms by filtration, while a porous plug that is made to be particularly effective from the point of view of retention of the ionic load, is still active in the destruction of the bacteria. These means reside in the configuration forming arches (13) around a central pad (11) and being arranged in the bottle (2) beyond its neck (10). These have been fully described in patent application WO 2011/095877. They contribute to an organization of the circulation of the fluids that is favourable to the requirements of the present invention in the case of the same liquids.

On the basis of tests completing the data from preliminary calculations, specifications will be determined on a case-by-case basis, to be met by the various elements involved in the migration of the active ions (in terms in particular of dimensions, porosity, composition of the material, initial concentration of labile ionic load), depending on the composition of the liquid to be expelled from the bottle, its physico-chemical characteristics, the level of sterility to be maintained, also depending on the conditions of use of the bottle and its useful life.

In practice, throughout the entire useful life of the bottle following its first use, the porous plug inside the nacelle forms an obstruction to the Ag ions coming from the membrane and at each step of dispensing of the liquid by expulsion of a drop of eye drops it becomes progressively impregnated with the active ions that have not been consumed, gradually over the layers through which the liquid passes. The biocidal agent is thus available there, to act both on the liquid and on the air within the porous material, and thus destroy the last organic contaminants that may still be present before they enter the liquid reserve that it is desired to keep sterile until the liquid is completely consumed.

At the same time, starting from a bottle the liquid dispensing head of which is provided with a tip made of polymer incorporating particles enclosing silver ions, the membrane is reloaded with silver ions during the different operations of dispensing a dose of liquid, when every time it allows an excess of non-expelled liquid which is returning to the bottle after having touched the material of the tip, to pass through. It has in fact been noted that here also, the gaseous flow of outside air entering the bottle consumes the positively-charged ions when it is in contact with the material, while when extracting the active ionic load from the material, the re-aspirated liquid phase flow tends to entrain it with itself rather than to consume it immediately in situ. As the membrane remains soaked with liquid from one dispensing operation to another, the ionic activity continues there, thanks to this repeated re-supply that reloads the membrane with biocidal ions.

By way of example, a bottle was used, made according to the invention, as has just been described for packaging eye drops, and different tests were carried out during the normal duration of use of the bottle, for a simulated consumption of one drop each morning and each evening, each dispensing dose being estimated at 30 microlitres for a bottle initially containing 10 millilitres of eye drops.

The measurements were repeated for several eye-drop solutions, each time determining the silver content of the liquid remaining available in the bottle firstly on opening the bottle (first use), then after one month's use of the bottle, then also after two months' use. With results always assessed at less than 0.1 µg/ml, it turns out that the values observed remain well below the requirements in practice for eye drops that do not contain an antibacterial preservative. There is no risk of irritation to the mucous membranes of the eye.

In completely different tests, the silver ion concentration existing within the porous plug present in the nacelle part of the device according to the invention was measured, after the plug had been cut into three disk sections once the eye drops had been consumed, simulating as before one drop morning and evening each day. It was clearly observed that on the one hand the silver content in the solid material of the plug decreases along the plug in its axial direction, from the outer layers through which the fluids enter on returning from a dispensing phase to the inner layers closer to the liquid reserve contained in the bottle, and that on the other hand it diminishes in each layer over time, which implies that the silver is consumed at each passage of the fluids through the bottle.

The above tests were carried out using a bottle equipped with a liquid dispensing head in which, according to the invention, the initial ionic charge in the membrane, expressed in weight of Ag+ or Ag++ element, was chosen comprised between 100 and 10,000 ppm for a membrane of 2.3 cm² in overall extent. Of course these are example cases, that can be adapted by modifying the estimated data depending on the conditions encountered in practice in each case of application of the invention.

The invention claimed is:

1. A device capable of dispensing liquid from a sterile bottle, comprising a bacteriological protection membrane (7) mounted across a duct capable of circulation of fluids between an inside and an outside of the bottle retain any microorganisms that may be present on the outside,
   wherein said membrane comprises a material incorporating an agent that is biocidally active by ionic oxidation, and said material comprising the membrane is made of a material having hydrophobic properties over a first part (22) of the extent of the membrane across said duct and having hydrophobic properties in a second part (23) of this extent,
   wherein said device comprises means for organizing the circulation of the air and liquid fluids through said membrane, said means for organizing comprising a porous plug (8) mounted across the duct capable of circulation of the fluids upstream of the membrane on the inside of the bottle, which is made of a material whose nature and porosity makes it capable of receiving and absorbing said biocidally active agent entrained by the liquid out of the membrane while avoiding its entry inside the bottle, said plug having multiple layers including outer layers and inner layers and an axial length determined so that the plug progressively collects the biocidally active agent starting with the outer layers, without reaching last inner layers throughout the entire period of use of the bottle until the liquid therein is completely consumed, and
   wherein the device comprises, downstream of the membrane on the outer side of the bottle, a tip capable of dispensing liquid from the bottle in successive doses, which is made of a non-porous polymeric material loaded with a biocidal agent of the same type as that present in said membrane and capable of migrating through the material of the tip to its free surface in order to be progressively released therefrom during the passage of the fluids, so that the excess that is not consumed on contact with the material of the tip is entrained with any liquid flow returning to the bottle, thus serving to re-load the membrane with biocidal agent.

2. The device according to claim 1, wherein said biocidally active agent is based on positively-charged metal ions.

3. The device according to claim 2, wherein said biocidally active agent is based on silver ions supported by a mineral macromolecular structure.

4. The device according to claim 1, wherein said membrane is made of a hydrophilic porous polymer substance loaded with an agent that is biocidal by ionic oxidation throughout its entire mass, said polymeric material then being rendered hydrophobic, locally throughout the entire thickness of the membrane over a part of the extent thereof across said duct by a polymerization treatment maintaining its biocidal activity.

5. The device according to claim 4, wherein said initially hydrophilic polymeric material is rendered locally hydrophobic by a radical cross-linking reaction between its constituents that is initiated by local irradiation of the membrane under ultraviolet radiation.

6. The device according to claim 5, wherein a hydrophobic part of the membrane is situated in a central zone of the membrane.

7. The device according to claim 1, wherein said means for organizing the circulation of the fluids also comprises, on an outer side of the membrane, respective means for guiding the air aspirated from the outside and any remaining liquid that has not been dispensed and is required to return to the bottle, which are configured so as to promote a biocidal effect on the aspirated airflow being exerted inside the membrane and to promote entrainment of the biocidal agent from the membrane by the flow of liquid passing therethrough.

8. The device according to claim 4, in which said membrane (7) is mounted between a nacelle (4) allowing sealed connection with the bottle and a tip (5) extending said nacelle out of the bottle, and in which said duct for the circulation of the fluids is restricted within said tip to a central channel (18) with a reduced cross-section for alternate circulation of the air and liquid fluids, wherein said means for organizing the circulation of the fluids also comprises, on an outer side of the membrane, respective means for guiding air aspirated from outside and any remaining liquid that has not been dispensed and is required to return into the bottle, which are configured so as to deflect towards the part of the extent of the membrane with hydrophilic properties any flow of liquid preceding the outside air into said channel and to facilitate the impact of the airflow on the part of the extent of the membrane with hydrophobic properties, the part of the extent of the membrane with hydrophobic properties being advantageously provided facing said channel for this purpose.

9. The device according to claim 8, wherein the means for guiding air aspirated from outside are arranged on the surface of a base of said tip facing the membrane, said means for guiding air aspirated from outside comprising radial slots with a wide cross-section arranged radiating about the nozzle of said channel and concentric circular grooves with a fine cross-section about said nozzle facing the hydrophobic part of the membrane.

10. The device according to claim 1, wherein the membrane has an average pore diameter adapted to the filtration of microorganisms having dimensions greater than a particle size of 0.3 to 1 µm.

11. The device according to claim 1, wherein the porous plug (8) is made so as to also act as a flow regulator contributing to the organization of the circulation of the fluids through said membrane.

12. The device according to claim 1, in which said plug is made of a fibrous hydrophobic material and has an equivalent average pore diameter of 20 to 120 micrometers.

13. The device according to claim 1, in which the material constituting said tip is based on polyethylene-type polymer.

14. The device according to claim 1, in which the material constituting said tip is based on polyethylene-type polymer and contains in its mass an agent with a biocidal effect by ionic oxidation in the form of Ag ions incorporated into mineral macromolecules.

15. The device according to claim 1, in which said tip is configured as a dropper tip, with a central channel with a capillary cross-section, opening to the outside of the bottle via a drop calibration orifice.

16. The device according to claim 15, wherein the central channel comprises a core dividing the flow circulating there.

17. The device according to claim 1, in a bottle capable of dispensing liquid in successive doses with a wall that can be reversibly elastically deformed by manual pressure, ensuring aspiration of outside air when the wall returns to its original shape after expulsion of a dose of liquid through the membrane under the effect of a manual pressure exerted on said wall.

18. The device according to claim 3, wherein the mineral macromolecular structure is a zeolite.

19. The device according to claim 1, wherein the membrane has an average pore diameter adapted to the filtration of microorganisms having dimensions greater than a particle size of 0.3 to 0.6 μm.

20. The device according to claim 16, wherein the core dividing the flow comprises a porous core (9), which comprises a material incorporating a biocidal agent in the form of silver ions on a support of mineral macromolecules.

* * * * *